(12) United States Patent
Wei et al.

(10) Patent No.: US 8,859,762 B2
(45) Date of Patent: Oct. 14, 2014

(54) METHODS FOR ULTRASONICATION-ASSISTED CHLORINATION OF AROMATIC COMPOUNDS

(75) Inventors: Yu Wei, Beijing (CN); Xiangyun Wang, Beijing (CN)

(73) Assignee: Peking University, Beijing (CN)

( * ) Notice: Subject to any disclaimer, the term of this patent is extended or adjusted under 35 U.S.C. 154(b) by 77 days.

(21) Appl. No.: 13/394,764

(22) PCT Filed: Nov. 26, 2010

(86) PCT No.: PCT/CN2010/079178
§ 371 (c)(1),
(2), (4) Date: Mar. 7, 2012

(87) PCT Pub. No.: WO2012/068740
PCT Pub. Date: May 31, 2012

(65) Prior Publication Data
US 2012/0277422 A1 Nov. 1, 2012

(51) Int. Cl.
*C07D 491/04* (2006.01)
*C07B 39/00* (2006.01)
*C07C 41/22* (2006.01)

(52) U.S. Cl.
CPC .............. *C07D 491/04* (2013.01); *C07B 39/00* (2013.01); *C07C 41/22* (2013.01)
USPC ......................................... 540/476; 570/246

(58) Field of Classification Search
None
See application file for complete search history.

(56) References Cited

U.S. PATENT DOCUMENTS

| | | | |
|---|---|---|---|
| 4,466,870 A | 8/1984 | Boudjouk et al. |
| 4,898,996 A | 2/1990 | Ishikura et al. |
| 5,732,073 A | 3/1998 | Kusaki et al. |
| 5,734,073 A | 3/1998 | Chambers et al. |
| 6,118,018 A | 9/2000 | Savidakis et al. |
| 6,124,512 A | 9/2000 | Cook et al. |
| 2009/0163741 A1 | 6/2009 | Meyer et al. |

FOREIGN PATENT DOCUMENTS

JP    2004-256500 A    9/2004

OTHER PUBLICATIONS

Martinez, A. et al., "Synthesis of Bridgehead Derivatives. 2. Preparation of 1-substituted Bicyclo[2.2.1] Heptanes," Synthesis, 1991, vol. 5, pp. 353-354.
International Search Report and Written Opinion for PCT/CN2010/079178, mailed Aug. 18, 2011.
Lu, H. et al. "Advance in Selective Chlorination of Aromatic Compounds," 2000, vol. 2, pp. 168-170.
Minero, C. et al., "Enhancement of Dye Sonochemical Degradation by Some Inorganic Anions Present in Natural Waters," Applied Catalysis, B: Environmental, 2008, vol. 77, No. 3-4, pp. 308-316.
Ranu, B. et al., "Direct Halogenation of Alcohols and Their Derivatives with Tert-Butyl Halides in the Ionic Liquid [pmIM] Br Under Sonication Conditions,—A Novel, Efficient and Green Methodology," European Journal of Organic Chemistry, 2005, vol. 4, pp. 755-758.
Tang, L.-T. et al., "A Density Functional Study on the Formation of Chare Transfer Complexes Between Alkaloids and Iodine Monochloride," Oct. 2004, vol. 686, No. 1-3, pp. 25-30.
Wei et al., "Iodination and radiolabeling of α-allocryptopine with iodine-125," Applied Radiation and Isotopes 62, 2005, pp. 55-62.

*Primary Examiner* — Noble Jarrell
(74) *Attorney, Agent, or Firm* — Foley & Lardner LLP

(57) ABSTRACT

Chlorinated aromatic compounds are prepared by ultrasonicating a mixture of ICl and an aromatic compound.

20 Claims, No Drawings

METHODS FOR ULTRASONICATION-ASSISTED CHLORINATION OF AROMATIC COMPOUNDS

CROSS-REFERENCE TO RELATED APPLICATIONS

This application is a national stage application of International Application Serial No. PCT/CN2010/079178, filed on Nov. 26, 2010, the entire disclosure of which is hereby incorporated by reference for all purposes in its entirety as if fully set forth herein.

TECHNICAL FIELD

The present technology generally relates to the use of sonication for use in the chlorination of organic compounds.

BACKGROUND

Chlorinated aromatic compounds are useful intermediates for the production of many pesticides, pharmaceuticals, and dyes. However, the yield and the selectivity of chlorination obtained from the existing aromatic compound-chlorinating reactions are poor. As chemical intermediates, most aromatic compounds have complex chemical structures, and factors such as spatial effects and inert substituents lead to harsh reaction conditions, low yield, and poor selectivity of chlorination.

Two methods are predominately used for the chlorination of aromatic compounds. The first method utilizes Lewis acids and sulfur compounds as catalysts. This method can improve the selectivity of chlorination of aromatic rings, but the difficult synthesis and identification of sulfur compounds limits the practical application of this method. The second method uses zeolite sieve catalysis technology, which enhances the yield and selectively of some chlorination reactions, yet some aromatic compounds cannot be chlorinated using the method.

SUMMARY

In one aspect, a method is provided for preparing a chlorinated aromatic compound. In some embodiments, the method includes ultrasonicating a mixture including iodine monochloride or $ICl_2(-)$ and an aromatic compound, where the chlorinated aromatic compound is prepared without preparing a significant amount of an iodinated aromatic compound; and the chlorinated aromatic compound is prepared at a higher yield than that without the ultrasonication. In some embodiments, the significant amount of an iodinated aromatic compound is less than about 10% on a molar basis. In some embodiments, the mixture includes iodine monochloride or $ICl_2^-$ and the aromatic compound in a molar ratio from about 1:1 to about 5:1. In some embodiments, the ultrasonicating is performed at a frequency of about 20 kHz to about 80 kHz. In some embodiments, the ultrasonicating is performed at a temperature of about 25° C. to about 100° C. In some embodiments, the ultrasonicating is performed for a period of about 15 minutes to about 4 hours.

In some embodiments, the mixture also includes a solvent. In some embodiments, the solvent is, for example, and without limitation, methylene chloride, chloroform, carbon tetrachloride, methanol, and ethanol.

In some embodiments, the aromatic compound includes an electron donating group, where the aromatic compound is chlorinated at a position that is para to the electron donating group. In some embodiments, the electron donating group is an alkoxy, hydroxy, amino, monoalkylamino, or dialkylamino group. In some embodiments, the electron donating group is an alkoxy group. In some embodiments, the aromatic compound is a phenylmethyl ether, an allocryptopine, or a salt thereof. In some embodiments, the aromatic compound is phenylmethyl ether, 2,4-dimethylphenylmethyl ether, 3,5-dimethylphenylmethyl ether, α-allocryptopine, or a salt thereof. In some embodiments, the chlorinated aromatic compound is 4-chlorophenylmethyl ether, or 12-chloro-α-allocryptopine or a salt thereof. In some embodiments, the chlorinated aromatic compound is 4-chlorophenylmethyl ether, 6-chloro-2,4-dimethylphenylmethyl ether, 5-chloro-2,4-dimethylphenylmethyl ether, 3-chloro-2,4-dimethylphenylmethyl ether, 4-chloro-3,5-dimethylphenylmethyl ether, or 12-chloro-α-allocryptopine or a salt thereof.

In some embodiments, the aromatic compound is a polycyclic aromatic compound. Examples of such polycyclic aromatic compounds include, without limitation, naphthalene, anthracene, phenanthrene, and the like.

DETAILED DESCRIPTION

In the following detailed description, the illustrative embodiments described are not meant to be limiting. Other embodiments may be utilized, and other changes may be made, without departing from the spirit or scope of the subject matter presented here.

As used herein, unless otherwise stated, the singular forms "a," "an," and "the" include plural reference.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

In one aspect, a method is provided for the selective chlorination of an aromatic compound comprising an electron donating group. As used herein, the term "selective chlorination" refers to the chlorination of the aromatic compound at a position on the aromatic ring that is both energetically and sterically favored. In some embodiments, such a favored position is para to the electron donating group on the aromatic compound. As used herein, the term "electron-donating group" refers to a group that causes an increase in electron density in the aromatic ring. Illustrative examples of electron-donating groups include, without limitation, alkyl, alkoxy, hydroxy, amino, monoalkylamino, and dialkylamino.

In one embodiment, the aromatic compound may comprise two alkoxy groups. In another embodiment, the two alkoxy groups together with the carbon atoms to which they are bonded form a 1,2 di-alkoxy group or a methylenedixoy or an ethylenedioxy group.

According to some embodiments, the method includes ultrasonicating the aromatic compound with iodine monochloride (ICl) in a single-phase, or multi-phase, mixture and ultrasonicating the mixture. One skilled in the art will appreciate that iodine dichloride ($ICl_2^-$) anion may also be suitably employed in accordance with the present methods. As a result of the ultrasonication, the aromatic compound is chlorinated at a higher yield, specifically at the para position of the aromatic compound in relation to the electron donating group. As used herein, "ultrasonication" refers to irradiation with ultrasonic (>20 kHz) waves. Ultrasonication may be performed using an ultrasonic bath or an ultrasonic probe.

In some embodiments, the aromatic compound is a polycyclic aromatic compound. Examples of such polycyclic aromatic compounds include, without limitation, naphthalene, anthracene, phenanthrene, and the like.

In one embodiment, the method provides an iodinated aromatic compound in an amount less than about 10% of the molar amount of the chlorinated aromatic compound. In another embodiment, the amount of the iodinated aromatic compound provided is less than about 5% of the molar amount of the chlorinated aromatic compound. In yet other embodiments, no iodinated aromatic compounds are isolated from the process. Comparatively, when the reaction is performed without ultrasonication, the iodinated aromatic compound is provided in a molar amount that is up to about twice the molar amount of the chlorinated aromatic compound. As used herein, the "chlorinated aromatic compound" contains at least one additional chlorine atom compared to the starting aromatic compound, and the additional chlorine atom is not part of a chloride or another anion. As used herein, the "iodinated aromatic compound" contains at least one additional iodine atom compared to the starting aromatic compound, and the additional iodine atom is not part of an iodide or another anion.

The aromatic compounds contacted may contain basic nitrogen atoms that, depending on their basicity, may combine with suitable acids, and form salts. Accordingly, the aromatic compounds may exist in such salt forms. Such salts, as will be apparent to the skilled artisan upon reading this disclosure, are also useful in the present methods.

The ICl or $ICl_2^-$ may be used in a ratio that is either equal to the aromatic compound on a molar basis, or is in excess. For example, in some embodiments, the ratio of ICl or $ICl_2^-$ to aromatic compound, on a molar basis, is about 1:1 to about 5:1. In another embodiment, the ratio on a molar basis, is about 2:1 to about 4:1. In another embodiment, the ratio on a molar basis, is about 4:1.

In another embodiment, the aromatic compound contacted is a benzo[c]phenanthridine alkaloid, such as, α-allocryptopine or a salt thereof. In another embodiment, the present technology provides 12-chloro-α-allocryptopine or a salt thereof prepared according to the methods of the present technology.

In another embodiment, the aromatic compound is a phenylalkyl ether. As used herein "a phenylalkyl ether" refers to an unsubstituted or substituted phenyl ring substituted with a alkoxy group. The alkoxy group may be any $C_1$-$C_{12}$ alkyl group, including, but not limited, methyl, ethyl, n-propyl, iso-propyl, n-butyl, iso-butyl, tert-butyl, etc. In some embodiments, the alkoxy group is methyl or ethyl. In some embodiments, the aromatic compound is phenylmethyl ether, 2,4-dimethylphenylmethyl ether, or 3,5-dimethylphenylmethyl ether.

Other suitable aromatic compounds that may be chlorinated in accordance with the present technology include, without limitation, other benzo[c]phenanthridine alkaloids. Such other suitable aromatic compounds having a =CH— moiety (or an unsubstituted carbon) para to an electron-donating group. Certain other benzo[c]phenanthridine alkaloids that may be chlorinated according to the present technology include, without limitation, berberine, chelerythrine, chelidonine, protopine and sanguinarine.

A variety of solvents may be employed in accordance with the present technology, depending, e.g., on the polar or non-polar nature of the organic compounds reacted. In certain embodiments, the aromatic compound is polar, and the solvent is a polar solvent. In certain embodiments, the aromatic compound is non-polar, and the solvent is a non-polar solvent. Illustrative non polar solvents include, but are not limited to, methanol, ethanol, dimethyl formamide, and tert-butyl methyl ketone, acetonitrile, acetone, tetrahydrofuran, and ethyl acetate. Compared to methanol, illustrative non-polar solvents include, but are not limited to, methylene chloride, chloroform, and carbon tetrachloride. In certain other embodiments, the reactions are carried out using a two-phase reaction system, wherein the aromatic compound dissolves in a first solvent phase and the chlorinating agent dissolves in a second solvent phase, and the first and second solvent phases phase separate. The ultrasonic treatment may promote mixing of the two-phase system and enhance the reaction efficiency. A skilled artisan, in view of this disclosure, will be able choose an appropriate solvent system for use in accordance with the present technology, based, for example, on solubility of reactants and other factors.

In another embodiment, the ultrasonication is performed at a frequency of about 20 kHz to about 80 kHz. In another embodiment, the ultrasonication is performed at a frequency of about 20 kHz, about 40 kHz, or about 80 kHz. A variety of ultrasonicators, that are commercially available, may be used for the ultrasonication in accordance with the present technology.

The reactions may be performed over a wide range of temperatures that are limited only by the solvent conditions or the stability of the reactants to heat. Thus, in some embodiments, the reactions are performed at a temperature of about 25° C. to about 100° C., or about 50° C. to about 75° C. In another embodiment, the ultrasonication is performed at about 40° C. When solvents having boiling points lower than about the contacting (or the reaction) temperatures are employed, the reaction may be performed in a vessel that can withstand pressure.

In another embodiment, the ultrasonication is performed for a period of about 5 minutes to about 24 hours, about 5 minutes to about 12 hours, and about 15 minutes to about 6 hours. In another embodiment, the ultrasonication is performed for about an hour. The skilled artisan upon reading this disclosure may also vary the ultrasonication period to a longer or a shorter period.

Compared to other known methods, the methods disclosed herein may provide one or more advantages including, but not limited to, improved reactivity and yields, increased reaction specificity (e.g., with respect to the type of halogenation, such as, chlorination over iodination), faster reaction times, and milder reaction conditions. For example, reaction yields may be improved by about 20% to about 80%, in accordance with the present technology compared to chlorination methods where ultrasonication is not employed.

As will be apparent to a skilled artisan, the $ICl_2(-)$ anion will be associated with a cation. Suitable cations useful in accordance with the present technology include without limitation, alkali metal cations, ammonium cations, and the like. Ammonium cations can further include tetraalkylammonium cations, which may make the corresponding $ICl_2(-)$ salt more soluble in an organic solvent, compared to an alkali metal salts. Suitable tetraalkylammonium cations include without limitation, benzyltrimethylamonium, benzyltriethylamonium, and tetrabutylammonium cations.

A skilled artisan, upon reading this disclosure, will appreciate that the chlorinated aromatic compounds may be separated from the reaction mixture and isolated in a pure form by employing one or more routine steps including, without limitation, aqueous work-up, chromatographic separation, and crystallization.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups.

As used herein, "alkoxy" refers to an —O-alkyl moiety. Examples of alkoxy groups include, without limitation, methoxy, ethoxy, isopropoxy, and benzyloxy. Examples of 1,2 di-alkoxy groups also include ring structures containing a methylenedioxy (—O—CH$_2$—O—) and an ethylenedioxy (—O—CH$_2$—CH$_2$—O—) moieties.

As used herein, "cycloalkyl" groups are monovalent cyclic hydrocarbons. Examples of cyloalkyl groups include, without limitation, cyclopropyl, cyclobutyl, cyclopentyl, and cyclohexyl. Cycloalkyl groups may be unsubstituted or substituted.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

In general, "substituted" refers to an organic group as defined herein (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; ethers; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. Aromatic groups may also be substituted by alkyl groups, or by two adjacent groups which together form a heteroatom containing ring.

The present technology, thus generally described, will be understood more readily by reference to the following example, which is provided by way of illustration and is not intended to limit the present technology.

EXAMPLES

α-Allocryptopine hydrochloride (1.1 mg, 2.9 μmol) and ICl (1.75 mg, 10.8 μmol) (molar ratio of about 1:4) were dissolved in CH$_2$Cl$_2$ (2 ml). The resulting solution was subjected to ultrasonication at 40° C. to 45° C. using an ultrasonic cleaner (TCQ-250, Beijing Second Medical Equipment Factory) under the "rigorous" mode (20 to 40 kHz) for 1 hour. HPLC and NMR analysis showed that only 12-chloro-α-allocryptopine was observed in a 70% yield. In comparison, when the above reaction was carried out in the absence of the ultrasonication for 3 days, the 12-chloro product was obtained in only 20% yield together with 20% of the 12-iodo-compound.

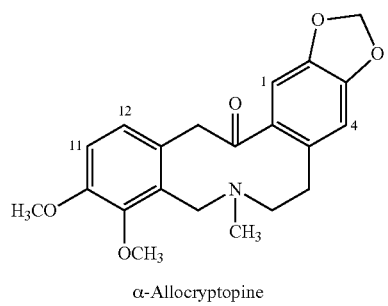 [SMILES: COc1ccc2c(c1OC)CN(C)CCc1cc3c(cc1C(=O)C2)OCO3]

α-Allocryptopine

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and compounds within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, or compounds, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

Other embodiments are set forth in the following claims.

What is claimed is:

1. A method of preparing a chlorinated aromatic compound comprising:
    ultrasonicating a mixture comprising ICl, $ICl_2^-$, or a mixture thereof; and an aromatic compound;
    wherein:
        the chlorinated aromatic compound is prepared without preparing an iodinated aromatic compound in an amount that is greater than about 10% on a molar basis; and
        the chlorinated aromatic compound is prepared at a higher yield than without ultrasonicating.

2. The method of claim 1, wherein the amount of an iodinated aromatic compound is less than about 5% on a molar basis.

3. The method of claim 1, wherein the amount of an iodinated aromatic compound is less than about 0.01% on a molar basis.

4. The method of claim 1, wherein no iodinated aromatic compounds are prepared.

5. The method of claim 1, wherein the mixture comprises iodine monochloride and the aromatic compound in a molar ratio from about 1:1 to about 5:1.

6. The method of claim 1, wherein the ultrasonicating is performed at a frequency of about 20 kHz to about 80 kHz.

7. The method of claim 1, wherein the ultrasonicating is performed at a temperature of about 25° C. to about 100° C.

8. The method of claim 1, wherein the ultrasonicating is performed for a period of about 15 minutes to about 4 hours.

9. The method of claim 1, wherein the mixture further comprises a solvent.

10. The method of claim 9, wherein the solvent comprises methylene chloride, methanol, or ethanol.

11. The method of claim 1, wherein the aromatic compound comprises an electron donating group, wherein the aromatic compound is chlorinated at a position that is para to the electron donating group.

12. The method of claim 11, wherein the electron donating group is an alkoxy, hydroxy, amino, monoalkylamino, or dialkylamino group.

13. The method of claim 11, wherein the electron donating group is an alkoxy group.

14. The method of claim 1, wherein the aromatic compound is a phenylalkyl ether, an allocryptopine, or a salt thereof.

15. The method of claim 14, wherein the aromatic compound comprises a phenylalkyl ether that is phenylmethyl ether, 2,4-dimethylphenylmethyl ether, or 3,5-dimethylphenylmethyl ether, or the aromatic compound is α-allocryptopine or a salt thereof.

16. The method of claim 14, wherein:
    the aromatic compound comprises a phenylalkyl ether and the chlorinated aromatic compound is 4-chloro-phenylmethyl ether, or
    the aromatic compound is α-allocryptopine and the chlorinated aromatic compound is 12-chloro-α-allocryptopine, or a salt thereof.

17. The method of claim 15, wherein:
    when the aromatic compound comprises a phenylmethyl ether, the chlorinated aromatic compound is 4-chlorophenylmethyl ether, 6-chloro-2,4-dimethylphenylmethyl ether, 5-chloro-2,4-dimethylphenylmethyl ether, 3-chloro-2,4-dimethylphenylmethyl ether, or 4-chloro-3,5-dimethylphenylmethyl ether, or
    when the aromatic compound is α-allocryptopine, the chlorinated aromatic compound is 12-chloro-α-allocryptopine or a salt thereof.

18. The method of claim 1, wherein the aromatic compound is a polycyclic aromatic compound.

19. The method of claim 18, wherein the polycyclic aromatic compound is naphthalene, anthracene, phenanthrene, or a salt thereof.

20. The method of claim 1, wherein the aromatic compound is berberine, chelerythrine, chelidonine, protopine, sanguinarine, or a salt thereof.

* * * * *

UNITED STATES PATENT AND TRADEMARK OFFICE
CERTIFICATE OF CORRECTION

PATENT NO. : 8,859,762 B2
APPLICATION NO. : 13/394764
DATED : October 14, 2014
INVENTOR(S) : Wei et al.

Page 1 of 1

It is certified that error appears in the above-identified patent and that said Letters Patent is hereby corrected as shown below:

On the Title Page, in item (56), under "OTHER PUBLICATIONS", in Column 2, Line 4, delete "Opinion for" and insert -- Opinion received for --, therefor.

In the Specification

In Column 1, Line 9, delete "application of" and insert -- application under 35 U.S.C. § 371 of --, therefor.

In Column 2, Line 52, delete "methylenedixoy" and insert -- methylenedioxy --, therefor.

In Column 3, Lines 43-44, delete "a alkoxy" and insert -- an alkoxy --, therefor.

In Column 4, Lines 56-57, delete "benzyltrimethylamonium, benzyltriethylamonium," and insert -- benzyltrimethylammonium, benzyltriethylammonium, --, therefor.

In Column 5, Line 17, delete "cyloalkyl" and insert -- cycloalkyl --, therefor.

Signed and Sealed this
Fourteenth Day of April, 2015

Michelle K. Lee
*Director of the United States Patent and Trademark Office*